United States Patent [19]

Mackey et al.

[11] Patent Number: 5,980,922
[45] Date of Patent: Nov. 9, 1999

[54] CLEANING ARTICLES TREATED WITH A HIGH INTERNAL PHASE INVERSE EMULSION

[75] Inventors: Larry Neil Mackey, Fairfield; Bryn Hird, Cincinnati; Paul Dennis Trokhan, Hamilton, all of Ohio

[73] Assignee: Procter & Gamble Company, Cincinnati, Ohio

[21] Appl. No.: 08/759,547

[22] Filed: Dec. 5, 1996

Related U.S. Application Data

[63] Continuation-in-part of application No. 08/640,268, Apr. 30, 1996, abandoned.

[51] Int. Cl.$^6$ .................................................. A01N 25/34
[52] U.S. Cl. ......................... 424/402; 424/404; 424/443
[58] Field of Search ................................... 424/402, 443, 424/404

[56] References Cited

U.S. PATENT DOCUMENTS

| | | | |
|---|---|---|---|
| 2,868,824 | 1/1959 | Haluska | 260/448.2 |
| 3,215,707 | 11/1965 | Rense | 260/326.3 |
| 3,231,587 | 1/1966 | Rense | 260/346.8 |
| 3,818,533 | 6/1974 | Scheuer | 15/104.93 |
| 3,819,530 | 6/1974 | Ratledge et al. | 252/311.5 |
| 3,847,637 | 11/1974 | Luszczak | 106/271 |
| 3,896,807 | 7/1975 | Buchalter | 128/261 |

(List continued on next page.)

FOREIGN PATENT DOCUMENTS

| | | | |
|---|---|---|---|
| 1 132 908 | 10/1982 | Canada | 167/310 |
| 0 110 678 A2 | 6/1984 | European Pat. Off. | C08K 7/00 |
| 0 259 034 A2 | 3/1988 | European Pat. Off. | A61K 7/00 |
| 0 365 160 A2 | 9/1989 | European Pat. Off. | A61K 7/40 |
| 0 501 791 A3 | 9/1992 | European Pat. Off. | C08G 77/46 |
| 0 545 002 A1 | 6/1993 | European Pat. Off. | C08G 77/46 |
| 0 631 774 A1 | 1/1995 | European Pat. Off. | A61K 9/113 |
| 2 321 389 | 12/1976 | France | B32B 29/02 |
| 3341770 A1 | 5/1985 | Germany. | |
| 155758 | 9/1981 | India. | |
| 2/152920 | 6/1990 | Japan. | |
| 3/168118 | 7/1991 | Japan. | |
| 05070337 | 3/1993 | Japan | A61K 7/48 |
| J5 9144-426 | 8/1994 | Japan. | |
| 1059541 | 2/1967 | United Kingdom. | |
| 2055689 | 3/1981 | United Kingdom | B32B 3/30 |
| 2 113 236 | 8/1983 | United Kingdom | C08L 83/12 |
| 87/03613 | 6/1987 | WIPO. | |
| 94/02120 | 2/1994 | WIPO. | |
| 95/16824 | 6/1995 | WIPO | D21H 17/14 |
| 96/14835 | 5/1996 | WIPO | A61K 9/70 |

OTHER PUBLICATIONS

"Dow Corning Q2–5200 Formulation Aid", Dow Corning Corporation (1990).

*Primary Examiner*—Jose' G. Dees
*Assistant Examiner*—Kathryne E. Shelborne
*Attorney, Agent, or Firm*—Carl J. Roof; E. Kelly Linman; Jacobus C. Rasser

[57] ABSTRACT

The invention relates to articles useful in cleansing, and particularly to wet-like cleansing wipes that are especially useful for hard surface cleaning, and in personal cleansing such as baby wipes and particularly for removal of perianal soils. These articles comprise: a carrier; and an emulsion applied to the carrier. The emulsion comprises (1) from about 2 to about 60% of a continuous solidified lipid phase comprising a waxy lipid material having a melting point of about 30° C. or higher, (2) from about 39 to about 97% of an internal polar (e.g., water) phase dispersed in the lipid phase; (3) an effective amount of a non-silicon containing emulsifier, where the emulsifier has a viscosity at 55° C. of greater than about 500 centipoise; and (4) and an optional second emulsifier having a viscosity at 55° C. of less than about 400 centipoise. Because the emulsion comprises a waxy external phase, the internal polar phase is retained in the emulsion until in-use shear pressures break the emulsion, thereby providing desired moisture for cleaning. The invention also relates to a process for making the cleaning articles.

49 Claims, 2 Drawing Sheets

U.S. PATENT DOCUMENTS

| | | | |
|---|---|---|---|
| 3,919,149 | 11/1975 | Cushman et al. | 260/28.5 AV |
| 3,965,518 | 6/1976 | Muoio | 15/104.96 |
| 3,982,993 | 9/1976 | Fife | 162/158 |
| 4,043,829 | 8/1977 | Ratledge et al. | 106/271 |
| 4,082,887 | 4/1978 | Coates | 428/289 |
| 4,104,403 | 8/1978 | Barker et al. | 424/365 |
| 4,112,167 | 9/1978 | Dake et al. | 428/154 |
| 4,117,199 | 9/1978 | Gotoh et al. | 428/486 |
| 4,122,029 | 10/1978 | Gee et al. | 252/309 |
| 4,137,358 | 1/1979 | Hartz | 428/272 |
| 4,203,877 | 5/1980 | Baker | 260/18 |
| 4,246,423 | 1/1981 | Martin | 556/423 |
| 4,293,611 | 10/1981 | Martin | 428/266 |
| 4,339,276 | 7/1982 | Yokoyama et al. | 106/271 |
| 4,377,649 | 3/1983 | Sweeney et al. | 524/49 |
| 4,381,241 | 4/1983 | Romenesko et al. | 252/8.5 P |
| 4,385,049 | 5/1983 | Cuca | 424/167 |
| 4,421,656 | 12/1983 | Donatelli et al. | 252/8.5 P |
| 4,446,051 | 5/1984 | Berthod et al. | 252/309 |
| 4,468,254 | 8/1984 | Yokoyama et al. | 106/271 |
| 4,481,243 | 11/1984 | Allen | 428/154 |
| 4,513,051 | 4/1985 | Lavash | 428/212 |
| 4,514,345 | 4/1985 | Johnson et al. | 264/22 |
| 4,520,160 | 5/1985 | Brown | 524/765 |
| 4,606,913 | 8/1986 | Aronson et al. | 424/59 |
| 4,698,178 | 10/1987 | Hüttinger et al. | 252/309 |
| 4,708,753 | 11/1987 | Forsberg | 149/2 |
| 4,782,095 | 11/1988 | Gum | 514/937 |
| 4,801,447 | 1/1989 | Gum | 424/68 |
| 4,844,756 | 7/1989 | Forsberg | 149/2 |
| 4,853,474 | 8/1989 | Bahr et al. | 556/445 |
| 4,875,927 | 10/1989 | Tadros | 71/94 |
| 5,021,405 | 6/1991 | Klimisch | 514/63 |
| 5,047,175 | 9/1991 | Forsberg | 252/356 |
| 5,133,972 | 7/1992 | Ferrini et al. | 424/449 |
| 5,136,068 | 8/1992 | Bahr et al. | 556/445 |
| 5,162,378 | 11/1992 | Guthauser | 514/785 |
| 5,210,102 | 5/1993 | Klimisch | 514/784 |
| 5,245,025 | 9/1993 | Trokhan et al. | 536/56 |
| 5,247,044 | 9/1993 | Crivello et al. | 528/15 |
| 5,277,761 | 1/1994 | Van Phan et al. | 162/109 |
| 5,292,503 | 3/1994 | Raleigh et al. | 424/59 |
| 5,362,482 | 11/1994 | Yoneyama et al. | 424/69 |
| 5,378,455 | 1/1995 | Kealey et al. | 424/73 |
| 5,387,417 | 2/1995 | Rentsch | 424/401 |
| 5,470,551 | 11/1995 | Dubief et al. | 424/70.12 |
| 5,482,703 | 1/1996 | Pings | 424/70.12 |
| 5,503,715 | 4/1996 | Trokhan et al. | 162/296 |
| 5,525,345 | 6/1996 | Warner et al. | 424/402 |
| 5,534,326 | 7/1996 | Trokhan et al. | 428/131 |
| 5,635,279 | 6/1997 | Ma et al. | 428/174 |

CLEANING ARTICLES TREATED WITH A HIGH INTERNAL PHASE INVERSE EMULSION

CROSS REFERENCE TO RELATED APPLICATION

This application is a continuation-in-part application of U.S. patent application Ser. No. 08/640,268, filed Apr. 30, 1996, now abandoned, by L. N. Macky et al.

TECHNICAL FIELD

This application relates to articles that are useful as wipes which are dry until used, but become wet during use. The application particularly relates to wet-like cleaning wipes that comprise a carrier treated with a high internal phase inverse emulsion comprising a continuous lipid external phase and a polar internal phase. The wipes are useful in various applications, including those for hard surface cleaning and personal cleansing such as baby wipes, and particularly for removal of perianal soils.

BACKGROUND OF THE INVENTION

Cleansing the skin is a personal hygiene problem not always easily solved. Of course, the common procedure of washing the skin with soap and water works well, but at times may be either unavailable or inconvenient to use. While soap and water could be used to clean the perianal region after defecation for example, such a procedure would be extremely burdensome. Dry tissue products are therefore the most commonly used post-defecation anal cleansing product in developed countries. These dry tissue products are usually referred to as "toilet tissue" or "toilet paper."

The perianal skin is marked by the presence of fine folds and wrinkles (sulci) and by hair follicles which make the perianal region one of the more difficult anatomical areas to cleanse. During defecation, fecal matter is excreted through the anus and tends to accumulate in hard to reach locations such as around the base of hairs and in the sulci of the skin's surface. As the fecal matter dehydrates upon exposure to the air, or upon contact with an absorbent cleansing implement such as tissue paper, it adheres more tenaciously to the skin and hair, thus making subsequent removal of the remaining dehydrated soil even more difficult.

Failure to remove fecal matter from the anal area can have a deleterious effect on personal hygiene. The fecal matter remaining on the skin after post-defecation cleansing has a high bacterial and viral content, is malodorous and is generally dehydrated. These characteristics increase the likelihood of perianal disorders and personal discomfort (e.g., itching, irritation, chafing, etc.). Further, the residual fecal matter stains undergarments and causes unpleasant odors to emanate from the anal region. Thus, the consequences of inadequate perianal cleansing are clearly unattractive.

For those individuals suffering from anal disorders such as pruritis ani, hemorrhoids, fissures, cryptitis, or the like, the importance of adequate perianal cleansing takes on heightened significance. Perianal disorders are usually characterized by openings in the skin through which the bacteria and viruses in the residual fecal matter can readily enter. Those people afflicted with anal disorders must, therefore, achieve a high degree of perianal cleansing after defecation or risk the likely result that their disorders will be aggravated by the bacteria and viruses remaining on the skin.

At the same time, anal disorder sufferers face more severe consequences from insufficient post defecation cleaning, they have greater difficulty in achieving a satisfactory level of soil removal. Anal disorders generally render the perianal region extremely sensitive and attempts to remove fecal matter from this region by wiping with even normal wiping pressure causes pain and can further irritate the skin. Attempts to improve soil removal by increasing the wiping pressure can result in intense pain. Conversely, attempts to minimize discomfort by reducing the wiping pressure result in an increased amount of residual fecal matter left on the skin.

Conventional toilet tissue products used for anal cleaning are essentially dry, low density tissue papers that rely exclusively on mechanical processes to remove fecal matter from the perianal skin. These conventional products are rubbed against the perianal skin, typically with a pressure of about 1 psi (7 kilopascals) and basically scrape or abrade the fecal matter from the skin. After the first few wipes, the upper portion of the soil layer is removed because the wiping process is able to overcome the soil-soil cohesive forces that exist within the fecal matter. A cleavage is thereby created in the soil layer itself with the upper portion of the fecal layer being removed and the lower portion of the soil remaining adhered to the perianal skin.

Conventional tissue products are absorbent and with each successive wipe the fecal matter becomes increasingly dehydrated, causing it to adhere more tenaciously to the perianal skin and hair and making its removal difficult in the extreme. Pressing the tissue forcefully against the perianal skin will remove more of the fecal matter but is intensely painful for people suffering from anal disorders and can excoriate even normal perianal skin, potentially causing irritation, inflammation, pain, bleeding, and infection.

To improve perianal cleaning, wipes have been developed that are kept in a dispenser and are typically soaked in a reservoir of a moistening solution. Examples of such products include wipes that are often used to clean babies after bowel movements and can have other additives in the moistening solution to soothe the skin. These wipes can have permanent wet strength such that they are not flushable. Also, these prior wipes are often too wet to dry the skin and tend to have a "cold" feel. There is also a lack of consistency in terms of the moisture content of each of the wipes.

Moistenable dry tissue products have also been used in perianal cleaning. These moistenable tissue products usually have temporary wet strength such that they are flushable. However, the users of these products have to separately wet the tissue, which can be inconvenient. It is also difficult to get the desired moisture level with such products. Also, the temporary wet strength of such products is typically inadequate and needs to be improved.

Accordingly, it would be desirable to provide products for cleaning, in particular personal cleansing, that: (1) have consistent levels of moistening solution; (2) can have adequate temporary wet strength so as to be flushable; (3) have an adequate, consistent moisture level to provide effective cleaning; and (4) remain essentially dry until used for cleaning purposes.

SUMMARY OF THE INVENTION

The present invention relates to articles useful in cleansing, and particularly to wet-like cleansing wipes that are especially useful for hard surface cleaning, and in personal cleansing such as baby wipes and particularly for removal of perianal soils. These articles comprise:

a. a carrier; and b. an emulsion applied to the carrier, the emulsion comprising:

(1) from about 2 to about 60% of a continuous solidified external lipid phase comprising a waxy lipid material having a melting point of about 30° C. or higher;

(2) from about 39 to about 97% of an internal polar phase dispersed in the external lipid phase;

(3) an effective amount of a non-silicon containing emulsifier capable of forming the emulsion when the external lipid phase is in a fluid state, wherein the emulsifier has a viscosity at 55° C. of greater than about 500 centipoise; and (4) optionally, a second emulsifier preferably having a lower viscosity than that of the first emulsifier.

The present invention further relates to a process for making these articles. This process comprises the steps of:

A. forming an emulsion comprising:

(1) from about 2 to about 60% of a continuous external lipid phase comprising a waxy lipid material having a melting point of about 30° C. or higher;

(2) from about 39 to about 97% of an internal polar phase dispersed in the external lipid phase;

(3) an effective amount of a non-silicon containing emulsifier capable of forming the emulsion when the external lipid phase is in a fluid state, wherein the emulsifier has a viscosity at 55° C. of greater than about 500 centipoise; and (4) optionally, a second emulsifier preferably having a lower viscosity than that of the first emulsifier;

B. applying the emulsion to a carrier at a temperature sufficiently high such that the external lipid phase has a fluid or plastic consistency; and C. cooling the applied emulsion to a temperature sufficiently low such that the external lipid phase solidifies.

These articles have a number of significant advantages over prior cleaning products, especially when in the form of wet-like cleansing wipes used to remove perianal soils, or when used as baby wipes. These articles release significant quantities of internal polar phase (e.g., and preferably, water/aqueous solutions) during use for comfortable, more effective cleaning. The continuous lipid phase of the emulsion is sufficiently brittle so as to be easily disrupted by low shear contact (e.g., during the wiping of the skin) to readily release this internal polar phase, but sufficiently tough to avoid premature release of the polar phase during the rigors of processing. The continuous lipid phase of these articles is also sufficiently stable during storage so as to prevent significant evaporation of the internal polar phase. The normal tensile strength and flushability properties of the articles are not adversely affected when treated with the high internal phase inverse emulsions of the present invention. As a result, users of these articles get comfortable, efficient, moist cleaning without having to change their normal cleaning habits.

Applicants have discovered that the use of a relatively high viscosity, non-silicon containing emulsifier(s) in formulating the high internal phase emulsion provides advantages over other emulsifiers. The emulsifiers provide better internal phase retention than lower viscosity emulsifiers, as well as the silicon-containing emulsifiers described in co-pending U.S. patent application Ser. No. 08/430,061, filed Apr. 27, 1995 by L. Mackey (Case 5653), particularly after being subjected to high shear processing conditions. This is beneficial in that the emulsions are preferably applied to the carrier using high shear dispersion.

Besides perianal cleaning, the present articles can be used in many other applications requiring the delivery of polar fluids such as water, as well as actives that are soluble or dispersible in polar fluids. Such applications include wipes for personal cleansing, such as baby wipes; as hard surface cleaners for floors, countertops, sinks, bathtubs, toilets, and the like; as well as for the delivery of polar-soluble or dispersible antimicrobial or pharmaceutical actives. The articles can also perform multiple functions. For example, the high internal phase inverse emulsion applied to the carrier can be formulated to provide concurrent cleaning and waxing benefits when the article is used on items such as furniture, shoes, automobiles, and the like.

DETAILED DESCRIPTION

Figure 1:
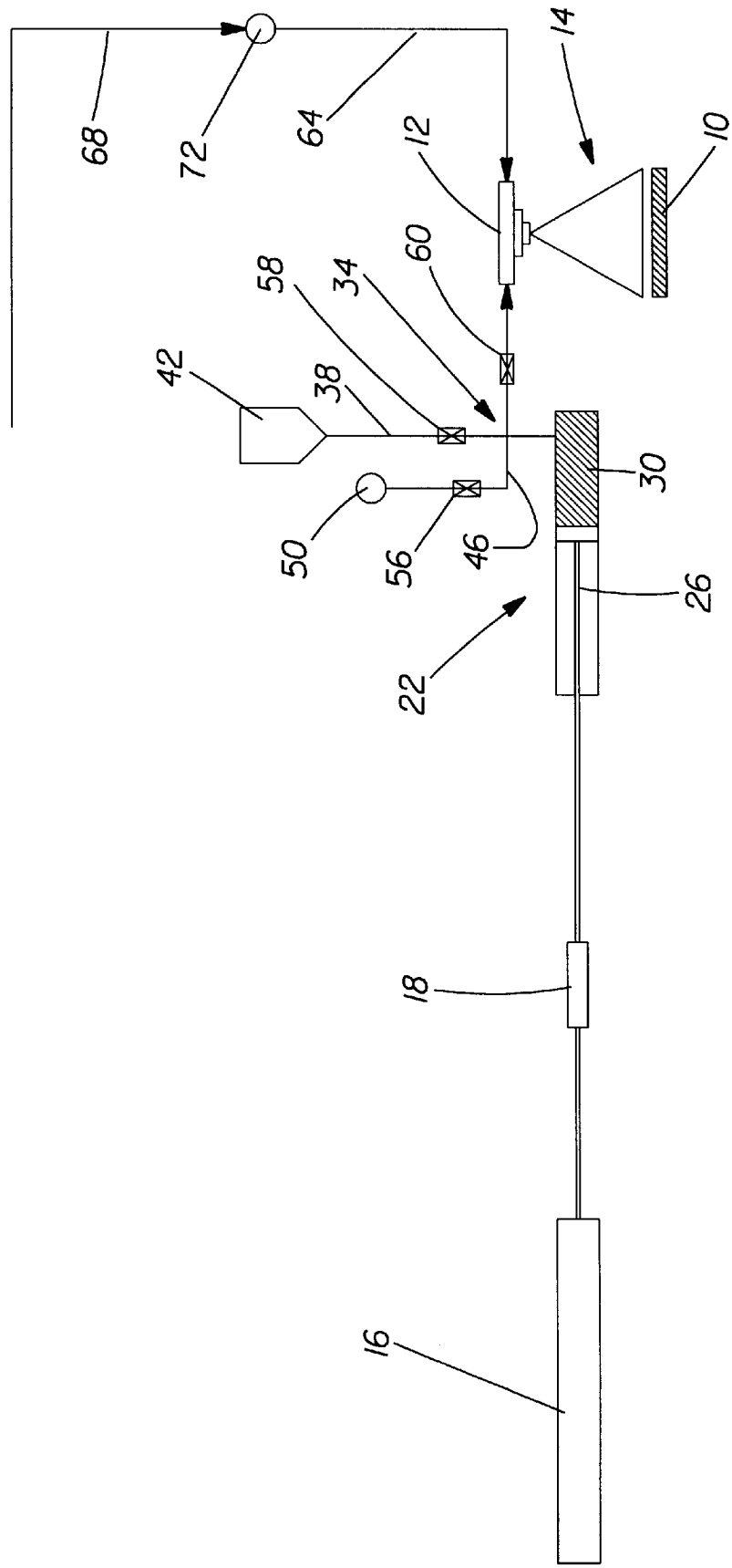
FIG. 1 is a schematic representation illustrating a spray system for applying the high internal phase inverse emulsions of the present invention to a carrier such as a paper web.

As used herein, the term "comprising" means that the various components, ingredients, or steps, can be conjointly employed in practicing the present invention. Accordingly, the term "comprising" encompasses the more restrictive terms "consisting essentially of" and "consisting of."

As used herein, the terms "detergent", "detersive surfactant" and "detergent surfactant" are used interchangeably, and refer to any substance that reduces the surface tension of water, specifically a surface-active agent which concentrates at oil-water interfaces, exerts emulsifying action, and thus aids in removing soils.

As used herein, the term "polar" means a molecule that possesses a dipole moment, i.e., a molecule of which the positive and negative electrical charges are permanently separated, as opposed to a nonpolar molecule in which the charges coincide. A "polar fluid" may comprise one or more polar constituents.

As used herein, the terms "substrate" and "layer", when used to describe the carriers of the present invention, refer to a component whose primary dimension is X-Y, i.e., along its length and width. It should be understood that the terms substrate and layer are not necessarily limited to single substrates/layers, or sheets, of material. Thus a substrate or layer can comprise laminates or combinations of several sheets or webs of the requisite type of materials. Accordingly, the term "substrate" includes "substrates", and the term "layer" includes the terms "layers" and "layered."

All percentages, ratios and proportions used herein are by weight unless otherwise specified.

A. Carriers for High Internal Phase Inverse Emulsion

Carriers useful in the present invention can be in a variety of forms. The carriers may comprise a single substrate, or a plurality of substrates. Of course, the desired end-use of the article will affect the particular carrier to be employed.

As used herein, the term "carrier" includes woven materials, nonwoven materials, foams, sponges, battings, balls, puffs, films, and the like. Particularly preferred substrates for use in the present invention are nonwoven types. These nonwoven substrates can comprise any conventionally fashioned nonwoven sheet or web having suitable basis weight, caliper (thickness), absorbency and strength characteristics. Nonwoven substrates can be generally defined as bonded fibrous or filamentous products having a web structure, in which the fibers or filaments are distributed randomly as in "air-laying" or certain "wet-laying" processes, or with a degree of orientation, as in certain "wet-laying" or "carding" processes. The fibers or filaments of such nonwoven substrates can be natural (e.g., wood pulp, wool, silk, jute, hemp, cotton, linen, sisal or ramie) or synthetic (e.g., rayon, cellulose ester, polyvinyl derivatives, polyolefins, polyamides or polyesters) and can be bonded together with a polymeric binder resin. Examples of suitable commercially available nonwoven substrates include those marketed under the tradename Sontara® by DuPont and Polyweb® by James River Corp.

For reasons of cost, ease of manufacture and article disposability (e.g., flushability), the preferred type of nonwoven substrate used in wipes of the present invention comprise those made from wood pulp fibers, i.e., paper webs. As noted, paper webs can be prepared by either air-laying or wet-laying techniques. Air-laid paper webs such as Air Tex® SC130 are commercially available from James River Corp.

More conventionally, paper webs are made by wet-laying procedures. In such procedures, a web is made by forming an aqueous papermaking furnish, depositing this furnish onto a foraminous surface, such as a Fourdrinier wire, and by then removing water from the furnish, for example by gravity, by vacuum assisted drying and/or by evaporation, with or without pressing, to thereby form a paper web of desired fiber consistency. In many cases, the papermaking apparatus is set up to rearrange the fibers in the slurry of papermaking furnish as dewatering proceeds in order to form paper substrates of especially desirable strength, hand, bulk, appearance, absorbency, etc.

The papermaking furnish utilized to form the preferred paper web substrates for articles of the present invention essentially comprises an aqueous slurry of papermaking fibers (i.e., paper pulp) and can optionally contain a wide variety of chemicals such as wet strength resins, surfactants, pH control agents, softness additives, debonding agents and the like. Wood pulp in all its variations can be used to form the papermaking furnish. Wood pulps useful herein include both sulfite and sulfate pulps, as well as mechanical, thermomechanical and chem-thermo-mechanical pulps, all of which are well known to those skilled in the papermaking art. Pulps derived from both deciduous or coniferous trees can be used. Preferably the papermaking furnish used to form the preferred paper web substrates for wipes of the present invention comprises Kraft pulp derived from northern softwoods.

A number of papermaking processes have been developed which utilize a papermaking apparatus that forms paper webs having particularly useful or desirable fiber configurations. Such configurations can serve to impart such characteristics of the paper web as enhanced bulk, absorbency and strength. One such process employs an imprinting fabric in the papermaking process that serves to impart a knuckle pattern of high density and low density zones into the resulting paper web. A process of this type, and the papermaking apparatus for carrying out this process, is described in greater detail in U.S. Pat. No. 3,301,746 (Sanford et al), issued Jan. 31, 1967, which is incorporated by reference.

Another papermaking process employs a throughdrying fabric having impression knuckles raised above the plane of the fabric. These impressions create protrusions in the throughdried sheet, and provide the sheet with stretch in the cross-machine direction. A process of this type is described in European Patent Publication No. 677,612A2, published Oct. 18, 1995 by G. Wendt et al., the disclosure of which is incorporated herein by reference.

Still another papermaking process carried out with a special papermaking apparatus, is one that provides a paper web having a distinct, continuous network region formed by a plurality of "domes" dispersed throughout the network region on the substrate. Such domes are formed by compressing an embryonic web as formed during the papermaking process into a foraminous deflection member having a patterned network surface formed by a plurality of discrete isolated deflection conduits in the deflection member surface. A process of this type, and apparatus for carrying out such a process, is described in greater detail in U.S. Pat. No. 4,529,480 (Trokhan), issued Jul. 16, 1985; U.S. Pat. No. 4,637,859 (Trokhan), issued Jan. 20, 1987; and; U.S. Pat. No. 5,073,235 (Trokhan), issued Dec. 17, 1991, all of which are incorporated by reference. Another type of papermaking process, and apparatus to carry it out that is suitable for making layered composite paper substrates is described in U.S. Pat. No. 3,994,771 (Morgan et al); issued Nov. 30, 1976, which is incorporated by reference.

The preferred paper web substrates can form one of two or more plies that can be laminated together. Lamination, and lamination carried out in combination with an embossing procedure to form a plurality of protuberances in the laminated product, is described in greater detail in U.S. Pat. No. 3,414,459 (Wells); issued Dec. 3, 1968, which is incorporated by reference. These paper substrates preferably have a basis weight of between about 10 $g/m^2$ and about 65 $g/m^2$, and density of about 0.6 g/cc or less. More preferably, the basis weight will be about 40 $g/m^2$ or less and the density will be about 0.3 g/cc or less. Most preferably, the density will be between about 0.04 g/cc and about 0.2 g/cc. See Column 13, lines 61–67, of U.S. Pat. No. 5,059,282 (Ampulski et al), issued Oct. 22, 1991, which describes how the density of tissue paper is measured. (Unless otherwise specified, all amounts and weights relative to the paper web substrates are on a dry basis.)

In addition to papermaking fibers, the papermaking furnish used to make these paper web substrates can have other components or materials added thereto as can be or later become known in the art. The types of additives desirable will be dependent upon the particular end use of the tissue sheet contemplated. For example, in wipe products such as toilet paper, paper towels, facial tissues, baby wipes and other similar products, high wet strength is a desirable attribute. Thus, it is often desirable to add to the papermaking furnish chemical substances known in the art as "wet strength" resins.

A general dissertation on the types of wet strength resins utilized in the paper art can be found in TAPPI monograph series No. 29, Wet Strength in Paper and Paperboard, Technical Association of the Pulp and Paper Industry (New York, 1965). The most useful wet strength resins have generally been cationic in character. For permanent wet strength generation, polyamide-epichlorohydrin resins are cationic wet strength resins that have been found to be of particular utility. Suitable types of such resins are described in U.S. Pat. No. 3,700,623 (Keim), issued Oct. 24, 1972, and U.S. Pat. No. 3,772,076 (Keim), issued Nov. 13, 1973, both of which are incorporated by reference. One commercial source of a useful polyamide-epichlorohydrin resin is Hercules, Inc. of Wilmington, Del., which markets such resins under the mark Kymene® 557H.

Polyacrylamide resins have also been found to be of utility as wet strength resins. These resins are described in U.S. Pat. Nos. 3,556,932 (Coscia et al), issued Jan. 19, 1971, and 3,556,933 (Williams et al), issued Jan. 19, 1971, both of which are incorporated by reference. One commercial source of polyacrylamide resins is American Cyanamid Co. of Stamford, Conn., which markets one such resin under the mark Parez® 631 NC.

Still other water-soluble cationic resins finding utility as wet strength resins are urea formaldehyde and melamine formaldehyde resins. The more common functional groups of these polyfunctional resins are nitrogen containing groups such as amino groups and methylol groups attached to nitrogen. Polyethylenimine type resins can also find utility in the present invention. In addition, temporary wet strength resins such as Caldas 10 (manufactured by Japan Carlit), CoBond 1000 (manufactured by National Starch and Chemical Company), and Parez 750 (manufactured by American Cyanamide Co.) can be used in the present invention. It is to be understood that the addition of chemical compounds such as the wet strength and temporary wet strength resins discussed above to the pulp furnish is optional and is not necessary for the practice of the present invention.

In addition to wet strength additives, it can also be desirable to include in the papermaking fibers certain dry strength and lint control additives known in the art. In this regard, starch binders have been found to be particularly suitable. In addition to reducing linting of the paper substrate, low levels of starch binders also impart a modest improvement in the dry tensile strength without imparting stiffness that could result from the addition of high levels of starch. Typically the starch binder is included in an amount such that it is retained at a level of from about 0.01 to about 2%, preferably from about 0.1 to about 1%, by weight of the paper substrate.

In general, suitable starch binders for these paper web substrates are characterized by water solubility, and hydrophilicity. Although it is not intended to limit the scope of suitable starch binders, representative starch materials include corn starch and potato starch, with waxy corn starch known industrially as amioca starch being particularly preferred. Amioca starch differs from common corn starch in that it is entirely amylopectin, whereas common corn starch contains both amylopectin and amylose. Various unique characteristics of amioca starch are further described in "Amioca—The Starch From Waxy Corn," H. H. Schopmeyer, Food Industries, December 1945, pp. 106–108 (Vol. pp. 1476–1478).

The starch binder can be in granular or dispersed form, the granular form being especially preferred. The starch binder is preferably sufficiently cooked to induce swelling of the granules. More preferably, the starch granules are swollen, as by cooking, to a point just prior to dispersion of the starch granule. Such highly swollen starch granules shall be referred to as being "fully cooked." The conditions for dispersion in general can vary depending upon the size of the starch granules, the degree of crystallinity of the granules, and the amount of amylose present. Fully cooked amioca starch, for example, can be prepared by heating an aqueous slurry of about 4% consistency of starch granules at about 190° F. (about 88° C.) for between about 30 and about 40 minutes. Other exemplary starch binders that can be used include modified cationic starches such as those modified to have nitrogen containing groups, including amino groups and methylol groups attached to nitrogen, available from National Starch and Chemical Company, (Bridgewater, N.J.), that have previously been used as pulp furnish additives to increase wet and/or dry strength.

The carriers of the present invention may also comprise one or more polarphobic (preferably hydrophobic) region(s). In preferred embodiments where the carrier comprises one or more hydrophobic regions, those regions can be generated by either 1) treating a hydrophilic substrate (described above) with a water repellent compound(s); or 2) using a hydrophobic material, such as a thin hydrophobic film or a layer of hydrophobic fibers, as a distinct layer. The preferred design of such articles will be a durable hydrophobic region which does not adversely affect the hand feel or softness of the carrier. Emulsion-treated carriers comprising a hydrophobic region and an optional substrate are described in co-pending U.S. patent application Ser. No. 08/759,546, now U.S. Pat. No. 5,763,332 filed Dec. 5, 1996 by Gordon et al. (P&G Case 6081R), the disclosure of which is incorporated herein by reference.

When forming the hydrophobic region via treatment of a substrate, the hydrophobic material is applied to the substrate by traditional spraying, coating or printing techniques and is then cured through heat and/or ultraviolet sources. (Surface treating with hydrophobic materials is described in co-pending U.S. patent application Ser. No. 08/442,935, filed May 31, 1995 by William R. Ouellette, et al., (Case 5337R2), which is incorporated herein by reference.) The resulting carrier has a substrate with at least one hydrophobic surface.

Numerous hydrophobic materials capable of being deposited on a substrate such as a nonwoven are known in the art and are useful herein. Preferred examples include a silicone material from Dow Corning of Midland, Mich. available as Syl-Off 7677 to which a crosslinker available as Syl-Off 7048 is added in proportions by weight of 100 parts to 10 parts, respectively. Another suitable surface treatment is a coating of a UV curable silicone comprising a blend of two silicones commercially available from General Electric Company, Silicone Products Division, of Waterford, N.Y., under the designations UV 9300 and UV 9380C-D1, in proportions by weight of 100 parts to 2.5 parts, respectively. Other suitable materials include, but are not limited to, fluorinated materials such as fluoropolymers (e.g., polytetrafluoroethylene (PTFE), commercially available under the trade name TEFLON®) and chlorofluoropolymers. Other materials which may prove suitable as the hydrophobic material are Petrolatum, latexes, paraffins, and the like, although silicone materials are preferred. Others include any of the commercial water repellents listed in McCutcheon's Volume 2: Functional Materials 1995, McCutcheon's Division, The Manufacturing Confectioner Publishing Co. (the disclosure of which is incorporated by reference herein), of which GrapHsize, available from Akzo Nobel Chemicals Inc., and Norgard 10-T, available from Norman, Fox & Co., are preferred. The necessary addition levels of the hydrophobic compound will be dependent on the substrate, but will generally fall within the range of from about 1% to about 10% add-on of the dry basis weight of the substrate layer.

The incorporation of a thin film or a layer of fibers to provide the optional hydrophobic region can be executed using any resin which can be extruded to form a hydrophobic film or layer of fibers. Resins useful in forming hydrophobic films/fibers include, but are not limited to, polyolefins such as polyethylene or polypropylene, polyacrylics, polyamides, polystyrenes, polyurethanes and the like. Most preferred are films (preferred) or fibers derived from polyolefins, preferably polyethylene or polypropylene. The film or fibers may be used as a flat sheet hydrophobic layer and can optionally be attached to a substrate by means of gluing, temperature bonding, or pressure bonding.

Due to the necessity for flexability of the wipe article to allow for better cleaning, it is desirable to mechanically treat hydrophobic thin films in such a way as to make them more flexible. Ring-rolling is an option which gives a film more flexibility. This technique is described in detail in, for example, U.S. Pat. Nos. 5,167,897 to Weber et al. and 5,366,782 to Curro et al., both of which are incorporated herein by reference. An alternative means for achieving flexibility is to utilize a hydrophobic structural elastic-like film (SELF) web. A structural elastic-like film web is an extensible material that exhibits an elastic-like behavior in the direction of elongation without the use of added elastic materials. SELF webs and techniques for obtaining "SELFed" films are described in the copending, commonly assigned U. S. patent application Ser. No. 08/203,456 entitled "Absorbent Article with Multiple Zone Structural Elastic-Like Film Web Extensible Waist Feature", filed by D. Roe, et al. on Feb. 24, 1994, which is incorporated herein by reference. In addition, a microapertured film allows flexability while maintaining a hydrophobic barrier against moderate pressure Preferred articles are those where the optional hydrophobic region is either a cross-linked silicone compound applied to all or a portion (preferably all) of one or both (preferably one) surfaces of the carrier, or a mechanically treated thin polymeric film such as ring rolled or SELFed polyethylene.

B. Composition of High Internal Phase Inverse Emulsion

The articles of the present invention comprise an emulsion that is applied to the carrier. This emulsion comprises: (1) a continuous solidified external lipid phase; (2) an internal polar phase dispersed in the external lipid phase; and (3) a non-silicon containing emulsifier having a viscosity at 55° C. of at least about 500 centipoise that forms the emulsion when the external lipid phase is fluid. Because the internal polar phase contains a high level of a polar material (s), this emulsion is typically referred to as a "high internal phase inverse emulsion". The high internal phase inverse emulsion ruptures when subjected to low shear during use, e.g., wiping of the skin or other surface, so as to release the internal polar phase.

1. External Lipid Phase

The continuous (external) solidified lipid phase provides the essential stabilizing structure for the high internal phase inverse emulsions of the present invention. In particular, this continuous lipid phase is what keeps the dispersed internal polar phase from being prematurely released prior to use of the article, such as during the rigors of processing.

The continuous lipid phase can comprise from about 2 to about 60% of the emulsion of the present invention. Preferably, this continuous lipid phase will comprise from about 5 to about 30% of the emulsion. Most preferably, this lipid phase will comprise from about 6 to about 15% of the emulsion.

The major constituent of this continuous lipid phase is a waxy lipid material. This lipid material is characterized by a melting point of about 30° C. or higher, i.e., is solid at ambient temperatures. Preferably, this lipid material has a melting point of about 50° C. or higher. Typically, this lipid material has a melting point in the range of from about 40° to about 80° C., more typically in the range of from about 60° to about 70° C.

Although this waxy lipid material is solid at ambient temperatures, it also needs to be fluid or plastic at those temperatures at which the high internal phase inverse emulsion is applied to the carrier substrate. Moreover, even though this lipid material is fluid or plastic at those temperatures at which the emulsion is applied to the carrier substrate, it should still desirably be somewhat stable (i.e., minimal coalescence of emulsion droplets ) for extended periods of time at elevated temperatures (e.g., about 50° C. or higher) that are normally encountered during storage and distribution of the articles of the present invention. This lipid material also needs to be sufficiently brittle at the shear conditions of use of the article such that it ruptures and releases the dispersed internal polar phase. These lipid materials should also desirably provide a good feel to the skin when used in personal care products such as wet-like cleansing wipes used in perianal cleaning.

Suitable waxy lipid materials for use in the high internal phase inverse emulsion of the present invention include natural and synthetic waxes, as well as other oil soluble materials having a waxy consistency. As used herein, the term "waxes" refers to organic mixtures or compounds that are generally insoluble in polar liquids such as water, and tend to exist as amorphous or microcrystalline solids at ambient temperatures (e.g., at about 25° C.). Suitable waxes include various types of hydrocarbons, as well as esters of certain fatty acids and fatty alcohols. They can be derived from natural sources (i.e., animal, vegetable or mineral) or can be synthesized. Mixtures of these various waxes can also be used.

Some representative animal and vegetable waxes that can be used in the present invention include beeswax, carnauba, spermaceti, lanolin, shellac wax, candelilla, and the like. Particularly preferred animal and vegetable waxes are beeswax, lanolin and candelilla. Representative waxes from mineral sources that can be used in the present invention include petroleum-based waxes such as paraffin, petrolatum and microcrystalline wax, and fossil or earth waxes such as white ceresine wax, yellow ceresine wax, white ozokerite wax, and the like. Particularly preferred mineral waxes are petrolatum, microcrystalline wax, yellow ceresine wax, and white ozokerite wax. Representative synthetic waxes that can be used in the present invention include ethylenic polymers such as polyethylene wax, chlorinated naphthalenes such as "Halowax," hydrocarbon type waxes made by Fischer-Tropsch synthesis, and the like. Particularly preferred synthetic waxes are polyethylene waxes.

Besides the waxy lipid material, the continuous lipid phase can include minor amounts of other lipophilic or lipid-miscible materials. These other lipophilic/lipid-miscible materials are typically included for the purpose of stabilizing the emulsion to minimize internal polar phase loss or improving the aesthetic feel of the emulsion on the skin. Suitable materials of this type that can be present in the continuous lipid phase include hot melt adhesives such as Findley 193-336 resin, long chain alcohols such as cetyl alcohol, stearyl alcohol, and cetaryl alcohol, water-insoluble soaps such as aluminum stearate, silicone polymers such as polydimethylsiloxanes, hydrophobically modified silicone polymers such as phenyl trimethicone, and the like. Other suitable lipophilic/lipid miscible materials include polyol polyesters. By "polyol polyester" is meant a polyol having at least 4 ester groups. By "polyol" is meant a polyhydric alcohol containing at least 4, preferably from 4 to 12, and, most preferably from 6 to 8, hydroxyl groups. Polyols include monosaccharides, disaccharides and trisaccharides, sugar alcohols and other sugar derivatives (e.g., alkyl glycosides), polyglycerols (e.g., diglycerol and triglycerol), pentaerythritol, and polyvinyl alcohols. Preferred polyols include xylose, arabinose, ribose, xylitol, erythritol, glucose, methyl glucoside, mannose, galactose, fructose, sorbitol, maltose, lactose, sucrose, raffinose, and maltotriose. Sucrose is an especially preferred polyol. With respect to the polyol polyesters useful herein, it is not necessary that all of the hydroxyl groups of the polyol be esterified, however disaccharides polyesters should have no more than 3, and more preferably no more than 2 unesterified hydroxyl groups. Typically, substantially all (e.g., at least about 85%) of the hydroxyl groups of the polyol are esterified. In the case of sucrose polyesters, typically from about 7 to 8 of the hydroxyl groups of the polyol are esterified.

By "liquid polyol polyester" is meant a polyol polyester from the hereinafter described groups having a fluid consistency at or below about 37° C. By "solid polyol polyester" is meant a polyol polyester from the hereinafter described groups having a plastic or solid consistency at or above about 37° C. As hereinafter described, liquid polyol polyesters and solid polyol polyesters may be successfully employed as emollients and immobilizing agents, respectively, in emulsions of the present invention. In some cases, solid polyol polyesters may also provide some emolliency functionality.

2. Internal Polar Phase

The major component of the high internal phase inverse emulsions of the present invention is typically the dispersed internal polar phase. This polar phase can provide a number of different benefits when released. For example, in preferred wet-like cleaning wipes for perianal cleaning, it is this released internal polar (preferably water) phase that provides the primary cleansing action for these wipes. In other products, this released internal polar phase can be used to deliver a variety of active components that are soluble or dispersible in the polar phase.

The internal polar phase can comprise from about 39 to about 97% of the emulsion incorporated into the articles of the invention. Preferably, this internal polar phase will comprise from about 67 to about 92% of the emulsion. Most preferably, this polar phase will comprise from about 82 to about 91% of the emulsion.

In preferred embodiments, the internal polar phase will comprise water as the main constituent. That is, the emulsion will be a water-in-lipid emulsion. In these preferred embodiments, the internal polar phase will contain a significant percentage of water, preferably at least about 60%, by weight of the internal polar phase, more preferably at least about 75%, by weight, still more preferably at least about 85%, by weight. In such embodiments, besides water, this internal water phase can comprise other water-soluble or dispersible materials that do not adversely affect the stability of the high internal phase inverse emulsion. One such material typically included in the internal water phase is a water-soluble electrolyte. The dissolved electrolyte minimizes the tendency of materials present in the lipid phase to also dissolve in the water phase. Any electrolyte capable of imparting ionic strength to the water phase can be used. Suitable electrolytes include the water soluble mono-, di-, or trivalent inorganic salts such as the water-soluble halides, e.g., chlorides, nitrates and sulfates of alkali metals and alkaline earth metals. Examples of such electrolytes include sodium chloride, calcium chloride, sodium sulfate, magnesium sulfate, and sodium bicarbonate. The electrolyte will typically be included in a concentration in the range of from about 1 to about 20% of the water phase.

Other water-soluble or dispersible materials that can be present in the internal water phase include thickeners and viscosity modifiers. Suitable thickeners and viscosity modifiers include water-soluble polyacrylic and hydrophobically modified polyacrylic resins such as Carbopol and Pemulen, starches such as corn starch, potato starch, tapioca, gums such as guar gum, gum arabic, cellulose ethers such as hydroxypropyl cellulose, hydroxyethyl cellulose, carboxymethyl cellulose, and the like. These thickeners and viscosity modifiers will typically be included in a concentration in the range of from about 0.05 to about 0.5% of the water phase.

Other water-soluble or dispersible materials that can be present in the internal water phase include polycationic polymers to provide steric stabilization at the water-lipid interface and nonionic polymers that also stabilize the water-in-lipid emulsion. Suitable polycationic polymers include Reten 201, Kymene® 557H and Acco 711. Suitable nonionic polymers include polyethylene glycols (PEG) such as Carbowax. These polycationic and nonionic polymers will typically be included in a concentration in the range of from about 0.1 to about 1.0% of the water phase.

In addition or alternative to containing water, the internal polar phase may comprise polar materials, including solvents such as ethanol, isopropanol, butanol and hexanol; glycols or substituted glycols such as propylene glycol, butylene glycol or hexylene glycol; polyglycols such as diethylene glycol or triethylene glycol; glycol ethers such as short chain (e.g., $C_1$–$C_6$) derivatives of oxyethylene glycol and oxypropylene glycol, such as mono- and di-ethylene glycol n-hexyl ether, mono-, di- and tri-propylene glycol n-butyl ether; and the like. Also, solvents such as tetrahydrofuran, dimethyl sulfoxide, acetone and the like may be included in the internal polar phase.

3. Emulsifier

Another key component of the high internal phase inverse emulsion of the present invention is an emulsifier. In the emulsions of the present invention, the emulsifier is included in an effective amount. What constitutes an "effective amount" will depend on a number of factors including the respective amounts of the lipid and polar phase components, the type of emulsifier used, the level of impurities present in the emulsifier, and like factors. Typically, the emulsifier comprises from about 1 to about 10% of the emulsion. Preferably, this emulsifier will comprise from about 3 to about 6% of the emulsion. Most preferably, this emulsifier will comprise from about 4 to about 5% of the emulsion.

While the singular "emulsifier" is used to describe this component, more than one emulsifier may be used when forming the emulsion. Indeed, as discussed below, it may be desirable to utilize two or more emulsifiers when certain materials are employed. Though not intended to limit the scope of the invention, where two emulsifiers are utilized, preferred is where the primary emulsifier comprises from about 1 to about 7%, more preferably from about 2 to about 5%, most preferably from about 2 to about 4%, by weight of the emulsion; and the secondary emulsifier comprises from about 0.5 to about 3%, more preferably from about 0.75 to about 2%, most preferably from about 0.75 to about 1.5%, by weight of the emulsion. (As used herein, the words "primary" and "secondary" relate to the relative levels of the two or more materials employed. As such, the required high viscosity material may be either a "primary" or a "secondary" emulsifier when combined with another emulsifier, depending on its level relative the other emulsifier(s).)

Applicants have found that utilization of non-silicon containing emulsifiers having a viscosity at 55° C. of at least about 500 centipoise provide emulsions that exhibit improved wet-retention properties over lower viscosity emulsifiers. Preferably, the high viscosity emulsifier has a viscosity at 55° C. of at least about 800 centipoise, more preferably at least about 1,500 centipoise, still more preferably about 5,000 centipoise, and most preferably at least about 10,000 centipoise. Typically, the emulsifier has a viscosity at 55° C. in the range of from about 500 to about 100,000 centipoise. Viscosity is measured using a Lab-Line Instruments Brookfield-type rotating disc viscometer with an L3 spindle at 6 revolutions per minute.

While not wishing to be bound by theory, it is believed that high viscosity emulsifiers increase the interfacial viscosity and provide mechanical stability to the emulsions to minimize coalescence.

The emulsifier needs to be substantially lipid-soluble or miscible with the lipid phase material, especially at the temperatures at which the lipid material melts. It also should have a relatively low hydrophilic-lipophilic balance, or HLB. Preferred emulsifiers have an HLB of less than about 5, preferably from about 1 to about 5. More preferred are emulsifiers having an HLB of from about 1.5 to about 3.5.

Preferred high viscosity emulsifiers useful in the present invention include those designated by The Lubrizol Corporation (Wickliffe, OH) as OS-122102, OS-121863, OS-121864, OS-80541J and OS-80691J. These emulsifiers are reaction products of (i) a hydrocarbyl-substituted carboxylic acid or anhydride (preferably a polyisobutylene-substituted succinic acid or anhydride), or a salt thereof; and (ii) an amine or an alcohol. The materials, and methods for their manufacture, are described in U.S. Pat. No. 4,708,753, issued Nov. 24, 1987 to Forsberg [see especially Column 3, lines 32–38; and Column 8, line 10, to Column 26, line 68], and U.S. Pat. No. 4,844,756, issued Jul. 4, 1989 to Forsberg, both of which are incorporated by reference herein.

Other materials believed to be useful as the high viscosity emulsifier in the present invention include hydrocarbon-substituted succinic anhydrides such as those described in U.S. Pat. No. 3,215,707, issued Nov. 2, 1965 to Rense; U.S. Pat. No. 3,231,587, issued Jan. 25, 1996 to Rense; U.S. Pat. No. 5,047,175, issued to Forsberg on Sep. 10, 1991; and World Patent Publication Number WO 87/03613, published by Forsberg on Jun. 18, 1987. These publications are all incorporated by reference herein.

Still other materials useful as the high viscosity emulsifier are ABA block copolymers of 12-hydroxystearic acid and polyethylene oxide. Such materials are described in U.S. Pat. No. 4,203,877, issued to A. S. Baker on May 20, 1980 and U.S. Pat. No. 4,875,927, issued to T. Tadros on Oct. 24, 1989, both of which are incorporated by reference herein. A representative material of this class useful as an emulsifier herein is available from Imperial Chemical Industries PLC as Arlacel P135.

While the above-described high viscosity, non-silicon containing materials may be used as a single emulsifier, it may be desired to employ more than one emulsifier when forming the emulsion. For example, where certain high viscosity emulsifiers are used, a certain "tacky" feel may result when the treated article is subjected to in-use shear pressures that break the emulsion. In this case, it may be desirable to use a relatively lower viscosity co-emulsifier with the high viscosity emulsifier, to allow use of a lower amount of the latter, thereby alleviating tackiness. The second emulsifier may be one of the "high viscosity" materials described above, or preferably, it will have a viscosity at 55° C. of less than 400 centipoise. The co-emulsifier may be either non-silicon containing or silicon containing.

In one preferred embodiment of the present invention, an emulsifier available from Lubrizol (i.e., reaction product of a polyisobutylene-substituted succinic acid and an amine) and a co-emulsifier that is an ABA block copolymer of poly-12-hydroxystearic acid and polyethylene oxide (e.g., ICI Arlacel P135) or a organopolysiloxane-polyoxyalkylene such as an alkyl dimethicone copolyol (e.g., Dow Corning Q2-5200 laurylmethicone copolyol), are used to provide an emulsion with improved water retention levels over time, as well as beneficial reduced tackiness (via reduction in level of high viscosity emulsifier). The skilled artisan will recognize that different desired end-uses will dictate whether multiple emulsifiers are appropriate, and the appropriate relative amounts of each if so. Such a determination will require only routine experimentation by the skilled artisan in view of the present disclosure.

4. Optional Emulsion Components

The high internal phase inverse emulsions used in the present invention can also comprise other optional components typically present in moisture containing solutions of this type. These optional components can be present in either the continuous lipid phase or the internal polar phase and include perfumes, antimicrobials (e.g., antibacterials), pharmaceutical actives, deodorants, opacifiers, astringents, skin moisturizers, and the like, as well as mixtures of these components. All of these materials are well known in the art as additives for such formulations and can be employed in effective, appropriate amounts in the emulsions of the present invention. A particularly preferred optional component that is included in the emulsions of wet-like cleansing wipes according to the present invention is glycerin as a skin conditioning agent.

The emulsion component of the articles of the present invention is described and claimed herein in terms of components (i.e., lipid phase components, internal polar phase components, emulsifier components, etc.), and corresponding amounts of these components, that are present after emulsion formation. That is, when the stable emulsion is formed and applied to the carrier. It is understood, however, that the description (components and amounts) of the emulsion also encompasses emulsions formed by combining the described components and levels, regardless of the chemical identity of the components after emulsification and application to the carrier.

C. Other Optional Wipe Components

Besides the high internal phase inverse emulsion, there are other optional components that can be included in the articles of the present invention, typically for the purpose of improving the cleaning performance of the article when the internal polar phase of the emulsion is released. Certain of these optional components cannot be present in the emulsion at significant levels (e.g., greater than 2% of the internal polar phase) because they can cause premature disruption of the emulsion. These include various anionic detergent surfactants that have relatively high HLB values (e.g., HLBs of from about 10 to about 25), such as sodium linear alkylbenzene sulfonates (LAS) or alkyl ethoxy sulfates (AES), as well as nonionic detergent surfactants such as alkyl ethoxylates, alkyl amine oxides, alkyl polyglycosides, zwitterionic detergent surfactants, ampholytic detergent surfactants, and cationic detergent surfactants such as cetyl trimethyl ammonium salts, and lauryl trimethyl ammonium salts. See U.S. Pat. No. 4,597,898 (Vander Meer), issued Jul. 1, 1986 (herein incorporated by reference), especially columns 12 through 16 for representative anionic, nonionic, zwitterionic, ampholytic and cationic detergent surfactants. Instead, these high HLB detergent surfactants can be applied or included in the article separately from the emulsion. For example, an aqueous solution of these high HLB detergent surfactants can be applied to one side of the carrier, with the high internal phase inverse emulsion being applied to the other side of the carrier. During wiping, the emulsion is disrupted, releasing the internal polar phase (e.g., water) so that it can then be combined with the high HLB detergent surfactant to provide improved cleaning.

Though the description of the invention generally relates to applying a single emulsion to the carrier, it is recognized that two or more different emulsions may be utilized in preparing a single article. In such embodiments, the emulsions may differ in a variety of ways, including but not limited to the ratio of the internal polar phase and the external lipid phase, the emulsifiers used, the components used for either or both of the internal and lipid phases, and the like. Utilization of multiple emulsions in one article may be particularly desirable when two or more components are incompatible with each other, but can each be included in a separate emulsion. Alternatively, if a particular reaction is desired at the time of use, the reactants can be provided in separate emulsions. Upon shearing of the emulsions during use, the desired reaction will occur. For example, where foaming is desired during the wiping processes, a mild acid can be incorporated in the internal polar phase of one emulsion, while bicarbonate is incorporated in the internal polar phase of a second emulsion. Upon shearing of the emulsions during use, the reactants interact to provide the desired foam.

D. Preparation of Emulsion Treated Articles

In preparing the articles according to the present invention, the high internal phase inverse emulsion is initially formulated. Typically, this is achieved by blending or melting together the lipid phase components and the emulsifier. The particular temperature to which this lipid/emulsifier mixture is heated will depend on the melting point of the lipid phase components. Typically, this lipid/emulsifier mixture is heated to a temperature in the range from about 60° to about 90° C., preferably from about 70° to about 80° C., prior to being mixed, blended or otherwise combined with the internal polar phase components. The melted lipid/emulsifier mixture is then blended with the polar phase components and then mixed together, typically under low shear conditions to provide the emulsion.

The resulting high internal phase inverse emulsion is then applied in a fluid or plastic state at the temperatures indicated above to the carrier, e.g., a paper web or a paper web laminated to a hydrophobic material. Any of a variety of methods that apply materials having a fluid or plastic consistency can be used to apply this emulsion. Suitable methods include spraying, printing (e.g., flexographic or screen printing), coating (e.g., gravure coating), extrusion, or combinations of these application techniques, e.g. spraying a detergent surfactant on the paper web, followed by gravure coating of the emulsion on the detergent treated web.

The emulsion can be applied either to one or both sides of the carrier, or, in the case of multi-ply webs, can be applied to the inner surface(s) of one or more of the plies. For example, in the case of a two ply carrier, the emulsion can be applied to the opposed inner surfaces of two paper webs, leaving the outside surfaces of the paper webs free of emulsion. Where application of the emulsion is to both sides of a paper web, application can be either sequential or simultaneous. Once the emulsion has been applied to the substrate, it is allowed to cool and solidify to form a solidified, typically discontinuous coating or film on the surface of the substrate.

When a paper web is used as the substrate, the high internal phase inverse emulsion is typically applied to the paper web after the web has been dried, i.e. a "dry web" addition method. The emulsion can also be applied nonuniformly to the surface(s) of the web. By "nonuniform" is meant that the amount, pattern of distribution, etc. of the emulsion can vary over the surface of the paper web. For example, some portions of the surface of the paper web can have greater or lesser amounts of the emulsion, including portions of the surface that do not have any emulsion on it. The high internal phase inverse emulsion can be applied to the paper web at any point after it has been dried. For example, the emulsion can be applied to the paper web after it has been creped from a Yankee dryer. Usually, it is preferred to apply the emulsion to the paper web as it is being unwound from a parent roll and prior to being wound up on smaller, finished product rolls.

In applying high internal phase inverse emulsions of the present invention to carriers, spray and gravure coating methods are usually preferred. FIG. 1 illustrates one such preferred method where the emulsion is sprayed onto a paper web 10. Referring to FIG. 1, this spray system has a spray head 12 that applies a dispersed spray 14 of the emulsion onto web 10.

This spray system is actuated by an assembly that consists of a ball screw drive 16 that is connected by coupling 18 to a piston 26 of hydraulic cylinder 22. A portion of cylinder 22 is shown in FIG. 1 as being filled with the high internal phase inverse emulsion as indicated by 30. Cylinder 22 is heated to keep emulsion 30 in a fluid or plastic state. Emulsion 30 enters cylinder 22 via a 4-way coupling 34 that has a line 38 connected to a heated filling port 42. Coupling 34 also has a line 46 that is connected to pressure gauge 50 and spray head 12. There are three valves indicated as 56, 58 and 60 that control the flow of the emulsion in lines 38 and 46. The spray system shown in FIG. 1 also has a line 64 connected to spray head 12 that allows air indicated generally as 68 to be admitted to the spray head. Line 64 also has a pressure gauge and regulator 72 for controlling and measuring the air pressure in line. Lines 64 and 46 are heated to maintain the emulsion in a molten state prior to application to the web.

To fill cylinder 22 with emulsion 30, valves 56 and 60 are closed and valve 58 is opened. Ball screw drive 16 is actuated so that piston 26 moves to the left. The vacuum created in cylinder 22 draws the emulsion from filling port 42 through line 38 and into cylinder 22. To provide emulsion from cylinder 22 to spray head 12, valve 58 is closed and valves 56 and 60 are opened. The ball screw drive 16 is actuated so that piston 26 moves to the right. This forces emulsion 30 out of cylinder 22 and into line 46 of coupling 34. The emulsion then passes through valve 60 and into the spray head 12 where it is dispersed by incorporation of air from line 64 to provide dispersed spray 14 that is then applied to web 10.

Figure 2:
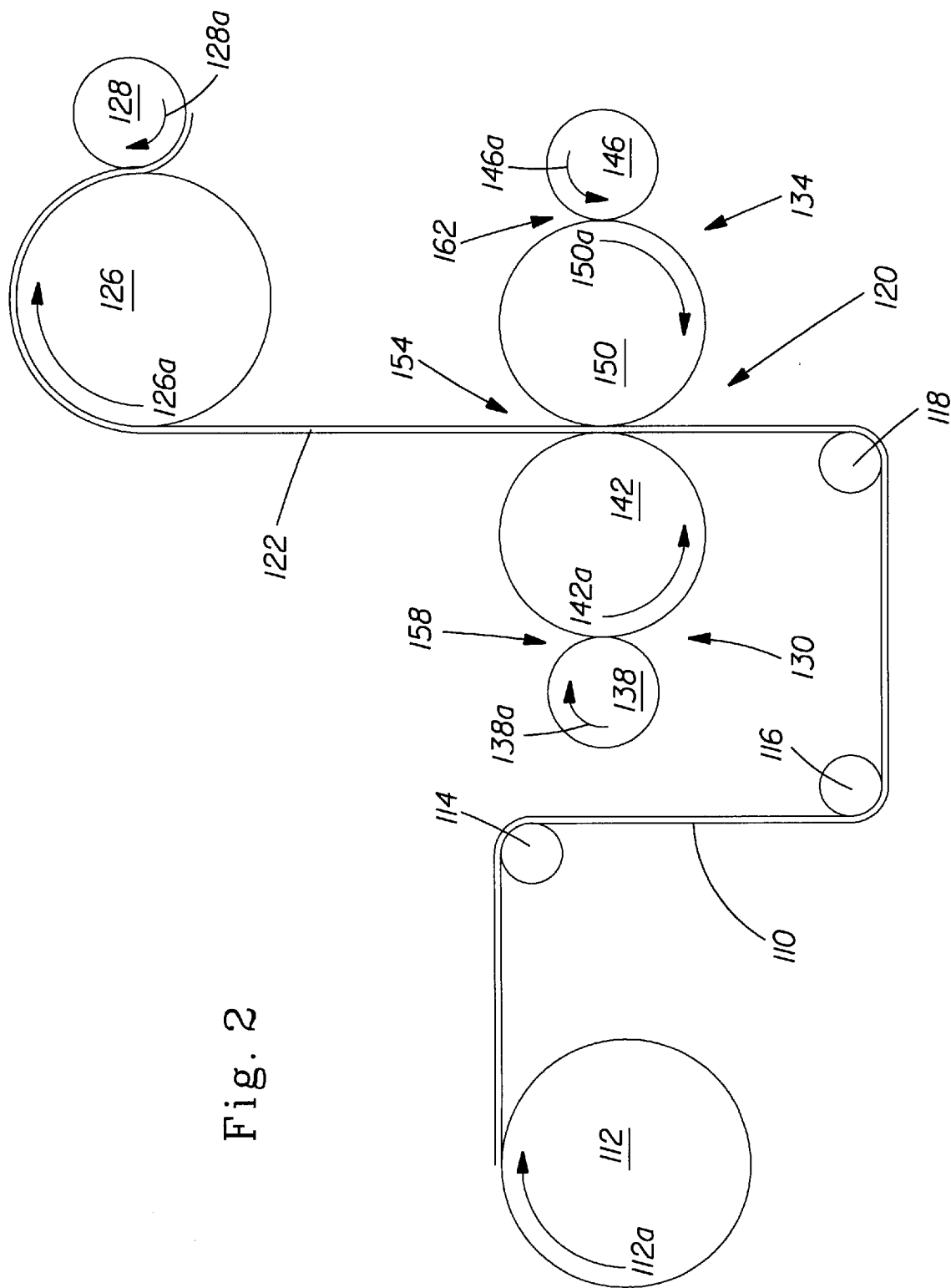
FIG. 2 is a schematic representation illustrating a system for applying the high internal phase inverse emulsions of the present invention by flexible rotogravure coating to a carrier such as a paper web.

FIG. 2 illustrates an alternative method for applying the high internal phase inverse emulsion involving a flexible rotogravure coating system. Referring to FIG. 2, a dried paper web 110 is unwound from parent tissue roll 112 (rotating in the direction indicated by arrow 112a) and advanced around turning rolls 114, 116 and 118. From turning roll 118, web 110 is advanced to a gravure coating station indicated generally as 120 where the emulsion is then applied to both sides of the web. After leaving station 120, web 110 becomes a treated web indicated by 122. Treated web 122 is advanced to surface rewinder roll 126 (rotating in the direction indicated by arrow 126a) and then wound up on finished product roll 128 (rotating in the direction indicated by arrow 128a).

Station 120 comprises a pair of heated linked gravure presses 130 and 134. Press 130 consists of a smaller anilox cylinder 138 and a larger print plate cylinder 142; press 134 similarly consists of a smaller anilox cylinder 146 and a larger print plate cylinder 150. Anilox cylinders 138 and 146 each have a ceramic or chrome surface, while print plate cylinders 142 and 150 each have a relief patterned rubber, urethane, or photopolymer surface. These anilox and print plate cylinders rotate in the directions indicated by arrows 138a, 142a, 146a and 150a, respectively. As shown in FIG.

2, print plate cylinders 142 and 150 are opposed to one another and provide a nip area indicated by 154 through which web 110 passes.

Hot, molten (e.g., 60° C.) emulsion is pumped to or sprayed onto each of these linked gravure presses 130 and 134 at the nip areas indicated by arrows 158 and 162, respectively, at a constant volumetric flow rate. (Emulsion delivered to presses 130 and 134 may be the same or different.) In other words, the emulsion is added to the linked gravure presses 130 and 134 at the same rate as the emulsion is being applied to the web 110. This eliminates emulsion "build-up" in the system. As anilox cylinders 138 and 146 rotate in the directions indicated by arrows 138a and 146a, they act as rotating doctor blades to spread the emulsion evenly across the surfaces of print plate cylinders 142 and 150, respectively, and to remove excess emulsion from the print plates of cylinders 142 and 150.

The emulsion that is spread onto print plate cylinders 142 and 150 (rotating in the opposite direction as indicated by arrows 142a and 150b) is then transferred to both sides of web 110 at nip area 154. The amount of the emulsion transferred to web 110 can be controlled by: (1) adjusting the width of nip area 154 between print plate cylinders 142 and 150; (2) adjusting the width of nip areas 158 and 162 between anilox/print plate cylinder pairs 138/142 and 146/150; (3) the print image relief (i.e., valley depth) of the print plate on cylinders 142 and 150; (4) the print area (i.e., valley area) of the print plate on cylinders 142 and 150; and/or (6) the print pattern of the print plate on cylinders 142 and 150.

Specific Illustrations of the Preparation of Wet-like Cleaning Wipes According to the Present Invention The following are specific illustrations of the preparation of wet-like cleaning wipes in accordance with the present invention by treating a carrier comprising tissue paper webs as the substrate with high internal phase inverse emulsions.

Example I—TOILET TISSUE

A) Emulsion Preparation

An emulsion is prepared from the ingredients shown in Table I.

TABLE I

|  | Amount (gm) | Percentage |
| --- | --- | --- |
| Lipid Phase Ingredients |  |  |
| Yellow Ceresine Wax (Strahl & Pitsch SP983) | 300 | 6% |
| Petrolatum (Fisher) | 100 | 2% |
| Lubrizol OS#121863 | 200 | 4% |
| Polar Phase Ingredients |  |  |
| Sodium Chloride (EM Science) | 50 | 1% |
| Dantogard (preservative from Lonza) | 25 | 0.5% |
| Distilled Water | 4325 | 86.5% |

In formulating the polar phase component, the sodium chloride and Dantogard are added to the distilled water and then heated to 160° F. (71.1 ° C.). The lipid phase ingredients and emulsifier (Yellow ceresine wax, petrolatum and Lubrizol OS#121863) are heated, with mixing to a temperature of about 170° F. (76.7° C.) until melted. The polar and lipid phase components are then combined in a stainless steel vessel and mixed with a Hobart Model 100-C mixer on the low speed setting while allowing the ingredients to cool slowly. Mixing is continued until the emulsion forms. Emulsion formation is evidenced by an increase in viscosity above 2000 centipoise as measured with a Lab-Line Instruments rotating disc viscometer with an L3 spindle at 6 revolutions per minute.

B) Applying Emulsion to Carrier

The emulsion can be applied to a tissue paper web using the spray system shown in FIG. 1. The emulsion is heated to temperature of 60° C. so that it is fluid or molten. The ball screw drive 16 moves at linear velocity of 0.002 in/sec as it actuates piston 26 (3.5 in. diameter) to push the emulsion out of cylinder 22 (emulsion pressure at about 12 psig). The emulsion enters spray head 12 (external mixing spray head with spray setup SUE15 from Spray Systems Inc., Wheaton, Ill.) and is dispersed in air (at 1.2 psig) heated to about 60° C. The emulsion is then applied from head 12 as a dispersed spray to the web while the web is being rewound at about 28 ft/min. For example, the web can be sprayed at the nip between a rewinder roll and finished product (such as at the nip between surface rewinder roll 126 and finished parent roll 128 shown in FIG. 2). As a result, the emulsion coats both sides of the web at about 50% add-on.

The emulsion can also be applied to a tissue paper web substrate using the flexible rotogravure coating system shown in FIG. 2. The hot, molten (e.g., 60° C.) emulsion is pumped to or sprayed onto each of these of linked gravure presses 130 and 134 at the nip areas indicated arrows by 158 and 162, respectively, at a constant volumetric flow rate of 20 ml/min. Anilox cylinders 138 and 146 spread the emulsion evenly across the surfaces of print plate cylinders 142 and 150, respectively (each rotating at about 40 feet/minute). Cylinders 142 and 150 then transfer the emulsion to both sides of web 110. The coated web 122 is transferred to surface rewinder roll 126 such that the coated central width of web 122 is over the depressed print area of roll 126. As a result, the coated central width of web 122 is not in contact with the surface of roll 126, while the noncoated edges of web 122 are in contact with the surface of roll 126. The web 122 is then wound up on finished product roll 128. The emulsion coats both sides of web 122 at about 50% add-on.

EXAMPLE I—TOILET TISSUE

This example illustrates preparation of an article comprising a paper substrate that is treated on one or both surfaces with a silicone polymer to provide phobic regions. The emulsion is added to either or both sides of the carrier.

A) Emulsion Preparation

An emulsion is prepared from the ingredients shown in Table II.

TABLE II

|  | Amount (gm) | Percentage |
| --- | --- | --- |
| Lipid Phase Ingredients |  |  |
| Yellow Ceresine Wax (Strahl & Pitsch SP983) | 24 | 8% |
| Petrolatum (Fisher) | 3 | 1% |
| Dow Corning Q2-5200 | 9 | 3% |
| Lubrizol OS#121863 | 3 | 1% |
| Arlamol ISML | 3 | 1% |
| Dow Corning 200 fluid 350cSt | 1.5 | 0.5% |
| Polar Phase Ingredients |  |  |
| 0.1% Carbopol 940 and | 259.5 | 85.5% |

TABLE II-continued

|  | Amount (gm) | Percentage |
|---|---|---|
| 0.05% Span 20 in distilled water adjusted to pH 6.0 with NaOH |  |  |

The lipid phase ingredients and emulsifier (yellow ceresine wax, petrolatum, Lubrizol OS#121863, Dow Corning Q2-5200, Arlamol ISML, and Dow Coming 200 fluid, 350 cSt) are heated and stirred in a 500 ml stainless steel beaker to a temperature of about 180° F. (82.8° C.) until melted. The polar phase component is added to the beaker containing the lipid phase component. The combined mixture is heated to 160° F. (71.1° C.) and then mixed with a "Lightnin' TS2510" mixer at 500 rpm while allowing the ingredients to cool until the emulsion forms.

B) Carrier Preparation

The carrier is formed by treating a substrate with a hydrophobic material. The substrate is a conventional tissue paper substrate. The base paper is a 70/30 Eucalyptus/NSK, non-layered sheet with a basis weight of 21.5 lbs/ream. This paper is unwound through a grauvure printing roll which applies Syloff 7677 polymer and Syloff 7048 crosslinker (Dow Corning) in a 95 to 5% blend. The Syloff mixture is applied at 5% of the dry substrate basis weight. This application is performed on only one side, or the carrier is passed through another printer to apply the same treatment to both sides of the carrier. The Syloff mixture is then cross-linked through the addition of heat by passing the carrier through two oven zones to provide hydrophobic regions to the carrier. The carrier is now ready for emulsion addition.

C) Applying Emulsion to Carrier

The emulsion prepared in Step A can be applied using the spray system shown in FIG. 1. The emulsion is heated to temperature of 60° C. so that it is fluid or molten. The ball screw drive 16 moves at linear velocity of 0.002 in/sec as it actuates piston 26 (3.5 in. diameter) to push the emulsion out of cylinder 22 (emulsion pressure at about 12 psig). The emulsion enters spray head 12 (external mixing spray head with spray setup SUE15 from Spray Systems Inc., Wheaton, Ill.) and is dispersed in air (at 1.2 psig) heated to about 60° C. The emulsion is then applied from head 12 as a dispersed spray to the carrier while the carrier is being rewound at about 28 ft/min. For example, the carrier can be sprayed at the nip between a rewinder roll and finished product (such as at the nip between surface rewinder roll 126 and finished parent roll 128 shown in FIG. 2). As a result, the emulsion coats both sides of the carrier at about 50% add-on, by dry weight of the carrier.

The emulsion can also be applied to the carrier using the flexible rotogravure coating system shown in FIG. 2. The hot, molten (e.g., 60° C.) emulsion is pumped to or sprayed onto each of these of linked gravure presses 130 and 134 at the nip areas indicated arrows by 158 and 162, respectively, at a constant volumetric flow rate of 20 ml/min. Anilox cylinders 138 and 146 spread the emulsion evenly across the surfaces of print plate cylinders 142 and 150, respectively (each rotating at about 40 feet/minute). Cylinders 142 and 150 then transfer the emulsion to both sides of carrier 11. The coated carrier 122 is transferred to surface rewinder roll 126 such that the coated central width of carrier 122 is over the depressed print area of roll 126. As a result, the coated central width of carrier 122 is not in contact with the surface of roll 126, while the noncoated edges of carrier 122 are in contact with the surface of roll 126. The carrier 122 is then wound up on finished product roll 128. The emulsion coats both sides of carrier 122 at about 50% add-on, by dry weight of the carrier, to provide an article of the present invention.

EXAMPLE III—TOILET TISSUE

A) Emulsion Preparation

An emulsion is prepared from the ingredients shown in Table III.

TABLE III

|  | Amount (gm) | Percentage |
|---|---|---|
| Lipid Phase Ingredients |  |  |
| Yellow Ceresine Wax (Strahl & Pitsch SP983) | 8 | 6% |
| Lubrizol OS# 122102 | 18 | 6% |
| Tween 60 (from ICI) | 0.9 | 0.3% |
| Polar Phase Ingredients |  |  |
| Distilled Water | 263.1 | 87.7% |

The lipid phase ingredients and emulsifier (yellow ceresine wax, Lubrizol OS#122102, and Tween 60) are heated to about 160° F. (71.1° C.) and mixed in a 500 ml stainless steel beaker until melted. The distilled water (polar phase) is added to the beaker containing the lipid phase ingredients. The mixture is heated to 160° F. (71.1° C.) and then mixed using a "Lightnin' TS2510" mixer at 500 rpm. The mixture is allowed to cool until the emulsion forms.

B) Applying Emulsion to Substrate

The emulsion is applied to a tissue paper web by either spraying or flexible rotogravure coating according to the procedures of Example I.

EXAMPLE IV—TOILET TISSUE

A) Emulsion Preparation

An emulsion is prepared from the ingredients shown in Table IV.

TABLE IV

|  | Amount (gm) | Percentage |
|---|---|---|
| Lipid Phase Ingredients |  |  |
| Paraffin wax (Aldrich) | 9 | 9% |
| Lubrizol OS# 122102 | 2 | 2% |
| Arlacel P135 | 2 | 2% |
| Polar Phase Ingredients |  |  |
| Sodium sulfate | 1 | 1% |
| Distilled Water | 86 | 86% |

The lipid phase ingredients and emulsifier (paraffin wax and Lubrizol OS#122102) are heated to about 140° F. (60° C.) and mixed in a 500 ml stainless steel beaker until melted. The remaining polar phase ingredients (sodium sulfate and distilled water) are added to the beaker containing the lipid phase ingredients. The mixture is heated to 140° F. (60° C.) and then mixed using a "Lightnin' TS2510" mixer at 500 rpm. The mixture is allowed to cool until the emulsion forms.

B) Applying Emulsion to Substrate

The emulsion is applied to a tissue paper web by either spraying or flexible rotogravure coating according to the procedures of Example I.

EXAMPLE V—BABY WIPE

This example illustrates preparation of an article comprising a polyethylene film (i.e., hydrophobic layer) treated on one side with an emulsion. This treated film is located between two paper substrates, to provide an article that is wetted on only one side when subjected to shear forces. The remaining dry side can absorb liquid remaining after use.

A) Emulsion Preparation

An emulsion (88% internal phase) is prepared from the ingredients in Table V.

TABLE V

|  | Amount (gm) | Percentage |
|---|---|---|
| Lipid Phase Ingredients |  |  |
| Yellow Ceresine Wax (Strahl & Pitsch SP983) | 18 | 6% |
| Petrolatum (Fisher) | 3 | 1% |
| White Ozokerite Wax (Strahl & Pitsch SP1190) | 6 | 2% |
| Lubrizol OS#121863 | 9 | 3% |
| Polar Phase Ingredients |  |  |
| 0.1% Carbopol 940* in distilled water adjusted to pH 6.0 with NaOH | 264 | 88% |

*Carbopol ® is an acrylate thickener available from B. F. Goodrich.

The lipid phase ingredients and emulsifier (yellow ceresine wax, petrolatum, white ozokerite wax and Lubrizol OS#121863) are heated and stirred in a 500 ml stainless steel beaker to a temperature of about 180° F. (82.8° C.) until melted. The internal polar phase component is prepared by adding 0.5 gm of Carbopol® 940 and 499.5 gm of distilled water to a 1 liter glass beaker, followed by mixing until the Carbopol® 940 is completely dissolved. The pH of this polar solution is adjusted to 6.0 with an appropriate amount of 1N NaOH. A portion (264 gm) of this polar solution is added to the beaker containing the lipid phase component. The combined mixture is heated to 160° F. (71° C.) and then mixed with a "Lightnin' TS2510" mixer at 500 rpm while allowing the ingredients to cool until the emulsion forms.

B) Emulsion Application/Carrier Preparation

The emulsion of Step A) is applied to one side of a hydrophobic, water impermeable film of ring rolled polyethylene, by either spraying or flexible rotogravure coating according to the procedures of Example I.

The emulsion-treated film is positioned between two hydroentangled substrate layers, each substrate being composed of about 40% natural fibers and about 60% polypropylene fibers (available from Fibertech). The overall basis weight of each of the two outer substrates is about 30 gsm.

The carrier is then passed through a printing station where a continuous coating of General Electric Co. UV9300 silicone release polymer and UV9310C photoinitiator in a ratio of 98/2. is applied. The carrier is then passed under a UV light source for cross-linking to form an article of the present invention.

EXAMPLE VI—HARD SURFACE WIPE CONTAINING AN ANTIMICROBIAL

A) Emulsion Preparation

An emulsion is prepared from the ingredients shown in Table VI and Table VI-a.

TABLE VI

| Lipid Phase Ingredients | Amount (gm) | Percentage |
|---|---|---|
| Yellow Ceresine Wax (Strahl & Pitsch SP983) | 18 | 6% |
| Petrolatum | 6 | 2% |
| Lubrizol OS# 12202 | 12 | 4% |
| Aqueous Phase (Described in Table VI-a) | 264 | 88% |

TABLE VI-1a

| Polar Phase Ingredients | Amount (gm) | Percentage of Total Emulsion |
|---|---|---|
| Hydrogen Peroxide (35% active from Sigma-Aldrich | 18 | 6% |
| Dequest 20605 (50% active from Monsanto Co.) | 1.2 | 0.4% |
| Isopropal Alcohol (from Sigma-Aldrich) | 45 | 15% |
| Eugenol (from Sigma-Aldrich) | 0.3 | 0.1% |
| Distilled Water | 199.5 | 66.5% |

The lipid phase ingredients and emulsifier (yellow ceresine wax, Petrolatum and Lubrizol OS#122102) are heated to about 160° F. (71.1° C.) and mixed in a 500 ml stainless steel beaker until melted. The polar phase materials are heated to 160° F. and mixed with a Greerco high shear mixer to form a dispersion. The polar phase is then added to the beaker containing the lipid phase ingredients and mixed using a "Lightnin' TS2510" mixer at 500 rpm. The mixture is allowed to cool until the antimicrobial emulsion forms.

B) Applying Emulsion to Substrate

The emulsion is applied to a tissue paper web by either spraying or flexible rotogravure coating according to the procedures of Example I.

EXAMPLE VII—HARD SURFACE WIPE CONTAINING AN ANTIMICROBIAL

A) Emulsion Preparation

An emulsion having 87% internal polar phase (consisting primarily of water) is prepared from the ingredients shown in Table VII.

TABLE VII

|  | Amount (gm) | Percentage |
|---|---|---|
| Lipid Phase Ingredients: |  |  |
| Strahl & Pitsch SP983 | 24 | 8.0 |
| Petrolatum | 6 | 2.0 |
| Lubrizol OS# 122102 | 9 | 3 |
| Polar Phase Ingredients: |  |  |
| Distilled Water | 617.76 | 77.22 |
| HEDP | 0.16 | 0.02 |
| Hydrogen Peroxide | 5.6 | 0.7 |
| Ethanol | 69.6 | 8.7 |
| C-12 Amine Oxide | 0.8 | 0.10 |
| Geraniol | 1.04 | 0.13 |
| Limonene | 0.52 | 0.065 |
| Eukalyptol | 0.52 | 0.065 |

To formulate the polar phase, all components are mixed together and then heated to 140° F. (45.8° C.). Separately, the lipid phase ingredients are heated, with mixing, to a temperature of about 140° F. until melted. The polar and lipid phase components are then combined in a stainless steel vessel and mixed with a Hobart Model 100-C mixer on the low speed setting while allowing the ingredients to cool slowly. Mixing is continued until the emulsion forms. Emulsion formation is evidenced by an increase in viscosity above 2000 centipoise as measured with a Lab-Line Instruments rotating disc viscometer.

B) Applying Emulsion to Carrier

The emulsion is applied to the carrier materials according to the description in Example V.

EXAMPLE VIII

A) Emulsion Preparation

A high internal phase emulsion (88.5% internal phase) is prepared from the ingredients shown in Table VIII.

TABLE VIII

|  | Amount (gm) | Percentage |
| --- | --- | --- |
| Lipid Phase Ingredients |  |  |
| Yellow Ceresine Wax (Strahl & Pitsch SP983) | 350 | 7% |
| Petrolatum (Fisher) | 50 | 1% |
| Lubrizol OS# 122102 | 150 | 3% |
| Arlacel P-135 emulsifier from ICI | 25 | 0.5% |
| Polar Phase Ingredients |  |  |
| Sodium Carbonate (anhydrous) | 25 | 0.5% |
| Dantogard (preservative from Lonza) | 25 | 0.5% |
| Denatured ethanol (3A from VRW Scientific) | 2000 | 40% |
| Distilled Water | 2375 | 47.5% |

In formulating the polar phase component, the Dantogard, sodium carbonate and ethanol are added to the distilled water and then heated to 160° F. (71.1° C.). Separately, the lipid phase ingredients (Yellow ceresine wax, petrolatum, emulsifier Lubrizol OS#122102 and emulsifier Arlacel P-135) are heated, with mixing, to a temperature of about 170° F. (77° C.) until melted. The polar and lipid phase components are then combined in a stainless steel vessel and mixed with a Hobart Model 100 C mixer on the low speed setting while allowing the ingredients to cool slowly. Mixing is continued until the emulsion forms. Emulsion formation is evidenced by an increase in viscosity above 2000 centipoise as measured with a Lab-Line Instruments rotating disc viscometer.

B) Applying Emulsion to Carrier

The emulsion can be applied to the carrier according to any of the procedures described in Examples I through VII.

What is claimed is:

1. An article, which comprises:
   a. a carrier; and
   b. a lipid continuous emulsion applied to the carrier, the emulsion comprising:
      (1) from about 2 to about 60% of a continuous solidified external lipid phase comprising a waxy lipid material having a melting point of about 30° C. or higher;
      (2) from about 39 to about 97% of an internal polar phase dispersed in the external lipid phase; and
      (3) an effective amount of a non-silicon containing emulsifier capable of forming the emulsion when the external lipid phase is in a fluid state; the emulsifier having a viscosity at 55° C. of at least about 500 centipoise.

2. The article of claim 1 wherein the internal polar phase comprises at least about 60%, by weight of the internal polar phase, of water.

3. The article of claim 2 wherein the internal polar phase comprises at least about 75%, by weight of the internal polar phase, of water.

4. The article of claim 3 wherein the internal polar phase comprises at least about 85%, by weight of the internal polar phase, of water.

5. The article of claim 1 wherein the emulsifier has a viscosity at 55° C. of at least about 1,500 centipoise.

6. The article of claim 5 wherein the emulsifier has a viscosity at 55° C. of at least about 5,000 centipoise.

7. The article of claim 6 wherein the emulsifier has a viscosity at 55° C. of at least about 10,000 centipoise.

8. The article of claim 5 wherein the emulsifier has an HLB of not more than about 5.

9. The article of claim 1 wherein the carrier comprises as a substrate layer a material selected from the group consisting of woven materials, nonwoven materials, foams, sponges, battings, balls, puffs, and films.

10. The article of claim 9 wherein the substrate layer is a paper web.

11. The article of claim 1 wherein the emulsion comprises from about 5 to about 30% of the external lipid phase and from about 67 to about 92% of the internal polar phase.

12. The article of claim 1 wherein the waxy lipid material has a melting point in the range of from about 40° to about 80° C.

13. The article of claim 1 wherein the waxy lipid material is selected from the group consisting of animal waxes, vegetable waxes, mineral waxes, synthetic waxes and mixtures thereof.

14. The article of claim 13 wherein the waxy lipid material is selected from the group consisting of beeswax, lanolin, candelilla, petrolatum, microcrystalline wax, yellow ceresine wax, white ozokerite, polyethylene waxes, and mixtures thereof.

15. The article of claim 1 wherein the carrier comprises two paper web plies having opposed inner surfaces and wherein the emulsion is applied to at least one of the opposed inner surfaces.

16. An article, which comprises:
   a. a carrier; and
   b. a lipid continuous emulsion applied to the carrier, the emulsion comprising:
      (1) from about 2 to about 60% of a continuous solidified external lipid phase comprising a waxy lipid material having a melting point of about 30° C. or higher;
      (2) from about 39 to about 97% of an internal polar phase dispersed in the external lipid phase; and
      (3) an effective amount of a non-silicon containing emulsifier capable of forming the emulsion when the external lipid phase is in a fluid state; wherein the emulsifier is a hydrocarbyl-substituted carboxylic acid or anhydride, or a salt, ester or amide thereof.

17. The article of claim 16 wherein the internal polar phase comprises at least about 60%, by weight of the internal polar phase, of water.

18. The article of claim 17 wherein the internal polar phase comprises at least about 75%, by weight of the internal polar phase, of water.

19. The article of claim 16 wherein the internal polar phase comprises at least about 85%, by weight of the internal polar phase, of water.

20. The article of claim 16, wherein the emulsifier is the reaction product of (i) a polyisobutylene-substituted carboxylic acid or anhydride, or a salt thereof; and (ii) an amine or an alcohol.

21. The article of claim 20, wherein the emulsifier is the reaction product of (i) a polyisobutylene-substituted succinic acid or succinic anhydride, or a salt thereof; and (ii) an amine or an alcohol.

22. The article of claim 16 wherein the emulsion comprises as a second emulsifier a block copolymer comprising poly-12-hydroxystearic acid and polyethylene oxide monomer units.

23. The article of claim 16, wherein the emulsion comprises as a second emulsifier an organopolysiloxane-polyoxyalkylene copolymer.

24. The article of claim 16 wherein the carrier comprises as a substrate layer a material selected from the group consisting of woven materials, nonwoven materials, foams, sponges, battings, balls, puffs, and films.

25. The article of claim 24 wherein the substrate layer is a paper web.

26. The article of claim 16 wherein the emulsion comprises from about 5 to about 30% of the external lipid phase and from about 67 to about 92% of the internal polar phase.

27. The article of claim 16 wherein the waxy lipid material has a melting point in the range of from about 40° to about 80° C.

28. The article of claim 16 wherein the waxy lipid material is selected from the group consisting of animal waxes, vegetable waxes, mineral waxes, synthetic waxes and mixtures thereof.

29. The article of claim 28 wherein the waxy lipid material is selected from the group consisting of beeswax, lanolin, candelilla, petrolatum, microcrystalline wax, yellow ceresine wax, white ozokerite, polyethylene waxes, and mixtures thereof.

30. An article, which comprises:
  a. a carrier; and
  b. an emulsion having a continuous external lipid phase and a dispersed polar internal phase applied to the carrier; wherein the emulsion is prepared by combining at least the following materials:
    (1) from about 2 to about 60% of a waxy lipid material having a melting point of about 30° C. or higher;
    (2) from about 39 to about 97% of polar material; and
    (3) an effective amount of a non-silicon containing emulsifier capable of forming the emulsion when the lipid is in a fluid state; the emulsifier having a viscosity at 55° C. of at least about 500 centipoise;
  where the weight percent for each of components (1), (2) and (3) is determined from the amount combined relative to the total weight of the emulsion.

31. The article of claim 30 wherein the polar material comprises at least about 60%, by weight of the polar material, of water.

32. The article of claim 31 wherein the polar material comprises at least about 75%, by weight of the polar material, of water.

33. The article of claim 32 wherein the polar material comprises at least about 85%, by weight of the polar material, of water.

34. An article, which comprises:
  a. a carrier; and
  b. a lipid continuous emulsion applied to the carrier, the emulsion comprising:
    (1) from about 2 to about 60% of a continuous solidified external lipid phase comprising a waxy lipid material having a melting point of about 30° C. or higher;
    (2) from about 39 to about 97% of an internal polar phase dispersed in the external lipid phase; and
    (3) an effective amount of a non-silicon containing emulsifier capable of forming the emulsion when the external lipid phase is a hydrocarbyl-substituted carboxylic acid or anhydride, or an ester or amide thereof;
  where the weight percent of each components (1), (2) and (3) is determined from the amount combined relative to the total weigh of the emulsion.

35. The article of claim 34 wherein the emulsion is prepared by further combining a second emulsifier, where the second emulsifier is a block copolymer comprising poly-12-hydroxystearic acid and polyethylene oxide monomer units.

36. The article of claim 34, wherein the second emulsifier is an organopolysiloxane-polyoxyalkylene.

37. A process for applying an emulsion to a carrier, which comprises the steps of:
  A. forming a lipid continuous emulsion comprising:
    (1) from about 2 to about 60% of a continuous solidified external lipid phase comprising a waxy lipid material having a melting point of about 30° C. or higher;
    (2) from about 39 to about 97% of an internal polar phase dispersed in the external lipid phase; and
    (3) an effective amount of a non-silicon containing emulsifier capable of forming the emulsion when the external lipid phase is in a fluid state; the emulsifier having a viscosity at 55° C. of at least about 500 centipoise;
  B. applying the emulsion to a carrier at temperature sufficiently high such that the external lipid phase has a fluid or plastic consistency; and
  C. cooling the applied emulsion to a temperature sufficiently low such that the external lipid phase solidifies.

38. The process of claim 37 wherein the emulsion is applied to the carrier at temperature in the range from about 60° to about 90° C.

39. The process of claim 38 wherein the emulsion is applied to the carrier at temperature in the range from 70° to about 80° C.

40. The process of claim 37 wherein the emulsion is applied to the carrier by a step selected from the group consisting of spraying, printing coating, extruding, and combinations thereof.

41. The process of claim 40 wherein the emulsion is applied to the carrier at a constant volumetric flow rate.

42. The process of claim 40 wherein the emulsion is applied to the carrier by flexible rotogravure coating.

43. The process of claim 37 wherein the carrier is a paper web.

44. The process of claim 43 wherein the emulsion is applied to both sides of the paper web simultaneously.

45. The process of claim 43 wherein the paper web comprises two plies having opposed inner surfaces and wherein the emulsion is applied to at least one of the opposed inner surface.

46. The process of claim 37 wherein the emulsion comprises from about 5 to about 30% of the external lipid phase and from about 67 to about 92% of the internal polar phase.

47. The process of claim 46 wherein the waxy lipid material is selected from the group consisting of animal waxes, vegetable waxes, synthetic waxes and mixtures thereof.

48. The process of claim 37 wherein the emulsifier comprises from about 1 to about 10% of the emulsion, and wherein the emulsifier has an HLB value in the range of from about 1.5 to about 3.5 and is non-silicon containing.

49. The process of claim 37 wherein the emulsifier is a hydrocarbon-substituted succinic anhydride or acid, or derivative thereof.

* * * * *